United States Patent [19]

Weinberger

[11] Patent Number: Plant 5,343

[45] Date of Patent: Nov. 20, 1984

[54] PLUM TREE, SUPLUMTHIRTEEN

[75] Inventor: John H. Weinberger, Fresno, Calif.

[73] Assignee: Superior Farming Company, Bakersfield, Calif.

[21] Appl. No.: 465,676

[22] Filed: Feb. 10, 1983

[51] Int. Cl.[3] ..... A01H 5/00

[52] U.S. Cl. ..... Plt./38

[58] Field of Search ..... Plt./38

*Primary Examiner*—James R. Feyrer

*Attorney, Agent, or Firm*—Huebner & Worrell

[57] ABSTRACT

A plum tree bearing fruit which ripens about one week after the Santa Rosa variety (unpatented) and about one week before the El Dorado variety (unpatented), the fruit of the new variety being globose, having a substantially black and uniform skin coloration, and having flesh of a uniform cream coloration.

1 Drawing Figure

BACKGROUND OF THE VARIETY

The present invention relates to a new and distinct variety of plum tree which has been named "Suplumthirteen" for commercial marketing. The new variety is distinguished by bearing fruit which is globose, has a black skin coloration, and has flesh of cream coloration, fruit of the present variety ripening about one week later than fruit of the Santa Rosa variety (unpatented) and about one week earlier than fruit of the El Dorado variety (unpatented).

The Santa Rosa variety of plum tree is probably the most important variety of plum tree heretofore grown in the San Joaquin Vally of California for commercial and home use. This variety bears fruit of small to medium size having a purplish-red skin coloration and having a flesh coloration which is yellow to dark red. Another important variety of plum tree is the El Dorado, which bears fruit of oblate shape and medium size having amber flesh coloration and reddish-black skin coloration. Fruit of the El Dorado variety ripens about two weeks later than fruit of the Santa Rosa variety. A factor favorably influencing the sale of fresh fruit is unusual, but attractive, skin and flesh coloration. Other such factors are regular shape, uniformity of coloration, and uniformity of shape and size. Therefore, a plum having a uniform, substantially black skin coloration, which has flesh of a contrasting and uniform cream color, and which is substantially uniformly of large size and globose shape, is especially advantageous.

ORIGIN AND ASEXUAL REPRODUCTION OF THE NEW VARIETY

The instant variety of plum tree was discovered on June 24, 1979 in a breeding orchard owned by Superior Farming Company, a corporation of the State of Nevada, in the course of a planned breeding program conducted by me for such company. This orchard is located at 5090 East Church Avenue, near the City of Fresno, in the County of Fresno, and in the State of Calif. In the breeding program, a plum tree, which was grown from a seedling of unknown variety, was open pollinated and the resulting seedlings planted and observed as they matured into trees and fruited. One of these trees proved advantageous and was selected as the subject variety. This tree was asexually reproduced under my direction in 1979 by budding on seedling rootstock and the resulting tree proved identical in tree and fruit characteristics to those of such selected tree.

SUMMARY OF THE NEW VARIETY

The instant variety of plum tree is characterized by bearing clingstone fruit of uniformly large size and uniform shape, and the instant variety is particularly characterized by its fruit ripening during a period between the ripening of fruit of the Santa Rosa variety and the ripening of fruit of the El Dorado variety and by the fruit of the new variety being globose, by having a skin of uniformly and substantially black coloration, and by having flesh of uniform cream coloration.

BRIEF DESCRIPTION OF THE DRAWING

The accompanying drawing is a color photograph of mature plums of the subject variety together with a typical twig showing characteristic leaves, one of the plums being divided in the suture plane to show the flesh and stone characteristics.

DETAILED DESCRIPTION

Referring more specifically to the pomological details of the new and distinct variety of plum tree, the following has been observed in the designated orchard in Fresno County, Calif. All of the color plate references are to the "Plochere Color System", published in Los Angeles, Calif., common descriptive color terms also being employed.

Tree: Medium size; medium vigor; productive; regular bearing; upright, open and round topped configuration.

Trunk: Medium thickness, medium texture.

Branches: Medium thickness; medium texture; dull grayish brown color.

Lenticels: Few, small.

Leaves:

*Length.*—90 mm.

*Width.*—27 mm.

*Size.*—Medium. Elliptic, medium thickness, medium color, smooth.

Margin: Crenate.

Petiole: Medium length and thickness.

Glands: Average 3 in number; alternate; medium size; globose, green in color; at base of leaf.

Stipules: Present.

Flower buds: Small, short, pointed, free.

Flowers: Date of full bloom: Mar. 3, 1981. Medium, small, white color.

Fruit: Described when firm and eating ripe on June 28, 1981. First commercial picking June 28, 1981; last commercial picking July 8, 1981. Size: Uniform, large.

*Diameter.*—Axial, 56 mm, transverse in suture plane, 60 mm.

*Form.*—Uniform, symmetrical, globose.

*Suture.*—An inconspicuous line, shallow, extends from base but discontinuous at apex.

*Ventral surface.*—Rounded slightly throughout both sides.

*Lips.*—Equal.

*Stem cavity.*—Rounded, elongated in suture plane with suture showing on one side. Depth: 6 mm. Breadth: 15 mm. Markings: none.

*Base.*—Rounded.

*Apex.*—Short, slightly depressed.

*Pistil point.*—Apical, round.

Skin: Medium thickness, medium toughness, tenaciously adherent to flesh.

*Tendency to crack.*—None in dry season.

*Color.*—Unpolished stem cavity — 497, Plate 21 "Hortensia". Skin with bloom removed — Black. Bloom — Gray.

*Down.*—Wanting.

Flesh:

*Color.*—Cream.

*Surface of pit cavity.*—Pale, 165 Plate 7 "Golden Peach".

*Amygdalin.*—Wanting.

*Juice.*—Moderate, rich.

*Texture.*—Medium, fine, melting.

*Fibers.*—Few, fine, tender.

*Ripening.*—Evenly.

*Flavor.*—Delicate.

*Aroma.*—Wanting.

*Eating quality.*—Best.

Stone: Cling, adheres to flesh over entire surface.

*Fibers.*—Short.

*Size.*—Medium.

*Length.*—22 mm.

*Breadth.*—17 mm.

*Thickness.*—10 mm.

*Form.*—Elliptical, cuneate toward base.

*Base.*—Straight.

*Hilum.*—Oblong.

*Apex.*—Acute.

*Sides.*—Equal.

*Surface.*—Regularly furrowed near base, pitted.

*Ridges.*—Rounded, continuous.

*Pits.*—Circular.

*Ventral edge.*—Thin, without wing.

*Dorsal edge.*—Narrow groove throughout.

*Color of stone.*—162 Plate 7, "Golden Tan".

*Tendency to split.*—Slight in dry season.

Use: Market

Keeping quality: Good.

Resistance to insects: Good.

Resistance to diseases: Good.

Shipping quality: Good.

Although the new variety of plum tree possesses the described characteristics as a result of the growing conditions in Fresno County, Calif. in the San Joaquin Valley, it is to be understood that variations of the usual magnitude in characteristics incident to growing conditions, fertilization, pruning and pest control are to be expected.

Having thus described and illustrated my new variety of plum tree, I claim:

1. A new and distinct variety of plum tree as described and illustrated, characterized by bearing clingstone fruit of relatively consistently large size and uniformly symmetrical shape and characterized as to novelty by bearing fruit which ripens about one week later than fruit of the Santa Rosa variety of plum tree (unpatented) and about one week before fruit of the El Dorado variety of plum tree (unpatented) and being further characterized as to novelty by bearing fruit during such period which has skin of a uniformly substantially black coloration, and which has flesh of a uniformly substantially cream coloration.

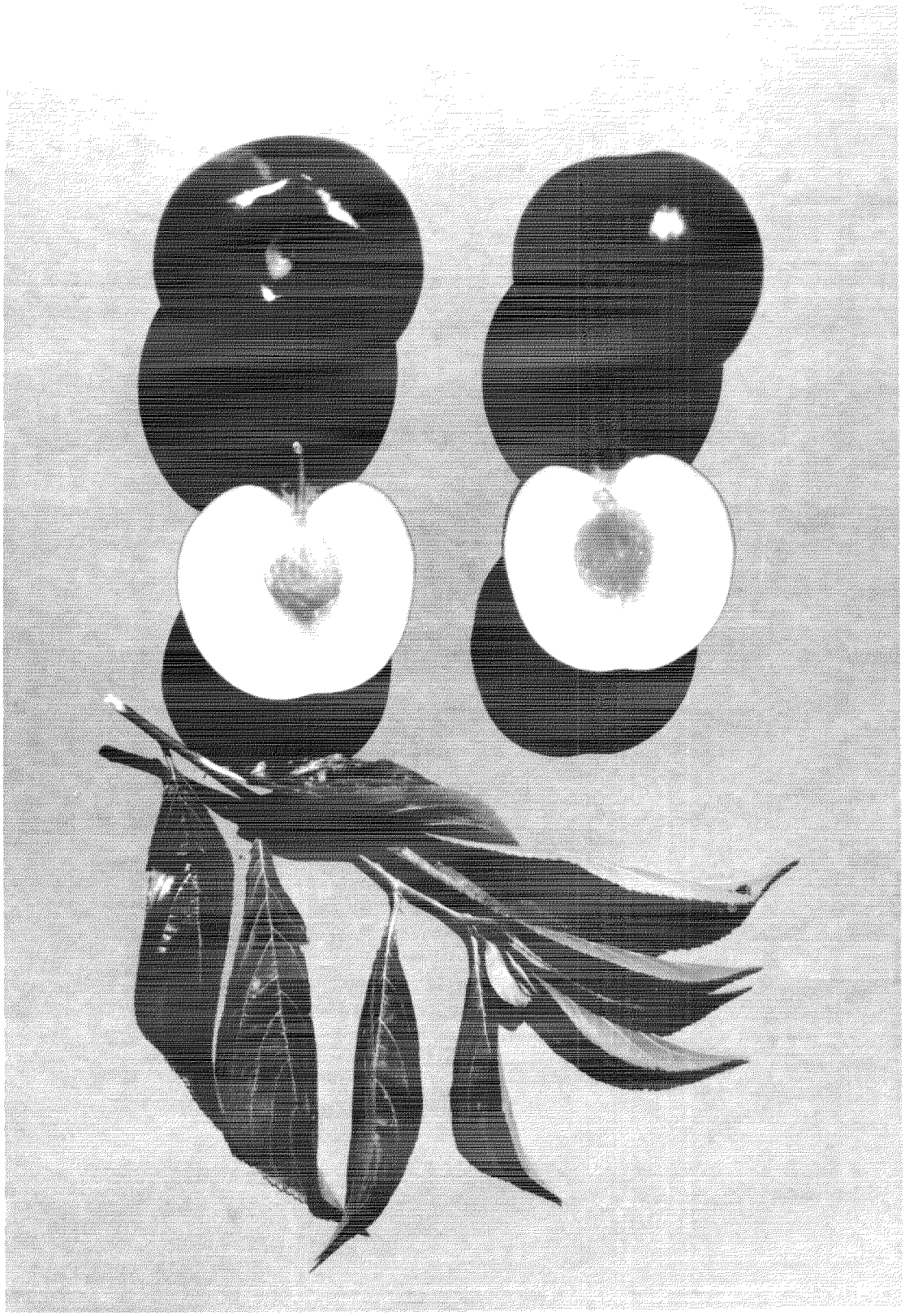

* * * * *